United States Patent [19]

Newton et al.

[11] Patent Number: 4,631,482
[45] Date of Patent: Dec. 23, 1986

[54] DUST FLOW INDUCING MONITOR

[75] Inventors: Robert E. Newton, Tewksbury; Russell S. Girgenti, South Hamilton, both of Mass.

[73] Assignee: Auburn International, Inc., Danvers, Mass.

[21] Appl. No.: 658,586

[22] Filed: Oct. 9, 1984

[51] Int. Cl.$^4$ ............................................. G01N 27/60
[52] U.S. Cl. .................................... 324/454; 340/627; 73/28
[58] Field of Search .................... 324/454, 464, 71.4, 324/65 R; 73/28, 432 PS, 861.63, 861.64, 861.73; 340/610, 627; 364/555; 361/229, 223; 417/197; 239/654, 117

[56] References Cited
U.S. PATENT DOCUMENTS

| 1,755,329 | 4/1930 | McCormack | 239/654 |
| 2,702,471 | 2/1955 | Vonnegut | 340/627 |
| 2,760,184 | 8/1956 | Beattie | 340/627 |
| 4,114,557 | 9/1978 | DeBrey | 73/28 |
| 4,192,461 | 3/1980 | Arborg | 417/197 |

Primary Examiner—Reinhard J. Eisenzopf
Assistant Examiner—Jack B. Harvey
Attorney, Agent, or Firm—Jerry Cohen; M. Lawrence Oliverio

[57] ABSTRACT

Airborne dust concentration in a silo or the like is measured by inducing flow in one or more Venturi nozzles (10) located in the area of airborne dust. A triboelectric sensor probe electrode (20) is located at the nozzle inlet section (12) and flow is induced by a feed of inductive air through an annular channel located in the wall of the nozzle downstream of the electrode.

3 Claims, 2 Drawing Figures

DUST FLOW INDUCING MONITOR

BACKGROUND OF THE INVENTION

The present invention relates to detection of gas borne fugitive dust concentrations and more particularly to determining a margin of safety relative to hazardous (explosive, suffocating, toxic, etc.) concentrations. The invention has application in grain silos, mineral storage bins, industrial process and heater exhaust ducts, freighter hulls, and other environments where dust concentration must be monitored and controlled. The invention is particularly characterized in affording an inexpensive, reliable measure of such concentration.

The grain industry, for example, is one that has been plagued by random situations of build-up of explosive concentrations of grain dust in storage silos.

It is the principal object of the invention to enable effective monitoring of dust concentrations in silos and the like.

SUMMARY OF THE INVENTION

In accordance with the invention sensor means are provided at one or more significant locations to produce localized acceleration of the air (or other gas medium) of a grain elevator or other enclosed volume. The conditions of acceleration are such that (a) the accelerated gas does not change its concentration of dust and (b) the velocity of gas is within a range for effective utilization of triboelectric charge transfer with respect to a sensing electrode in the accelerated gas stream. The acceleration is produced in a sensing assembly which consists of a venturi type compressed air (or other inert gas) driven inductor which causes a representative sample of the local chamber air to continuously pass through the sensing assembly. An electrode is located in the throat (smallest diameter) portion of the inductor to insure maximum velocity past the electrode. The dust particles rubbing the surface of the electrode cause a small charge transfer to occur between the electrode and the particle.

The charge imparted to the electrode is conducted to Earth through electronic control circuitry via an interconnecting shielded cable. The front end of the electronic control circuitry is an adjustable sensitivity current-to-voltage conversion circuit, whose sensitivity is adjustable over a one hundred to one range. The circuit is constructed with current limiting resistors to produce intrinsic safety at the sensing electrode.

A second stage of the circuit provides rectification since either polarity of the charge transfer could occur at the sensing electrode. The rectification is followed by an adjustable time constant to remove background noise. When the average signal exeeds a given (e.g., 3 volt) threshold, an alarm relay is energized, which may in turn, sound an alarm, start vent fans or shut-down a process.

Other objects, features and advantages will be apparent from the following detailed description of preferred embodiments thereof taken in connection with the accompanying drawings in which:

DETAILED DESCRIPTION OF PREFERRED EMBODIMENTS

Figure 1:
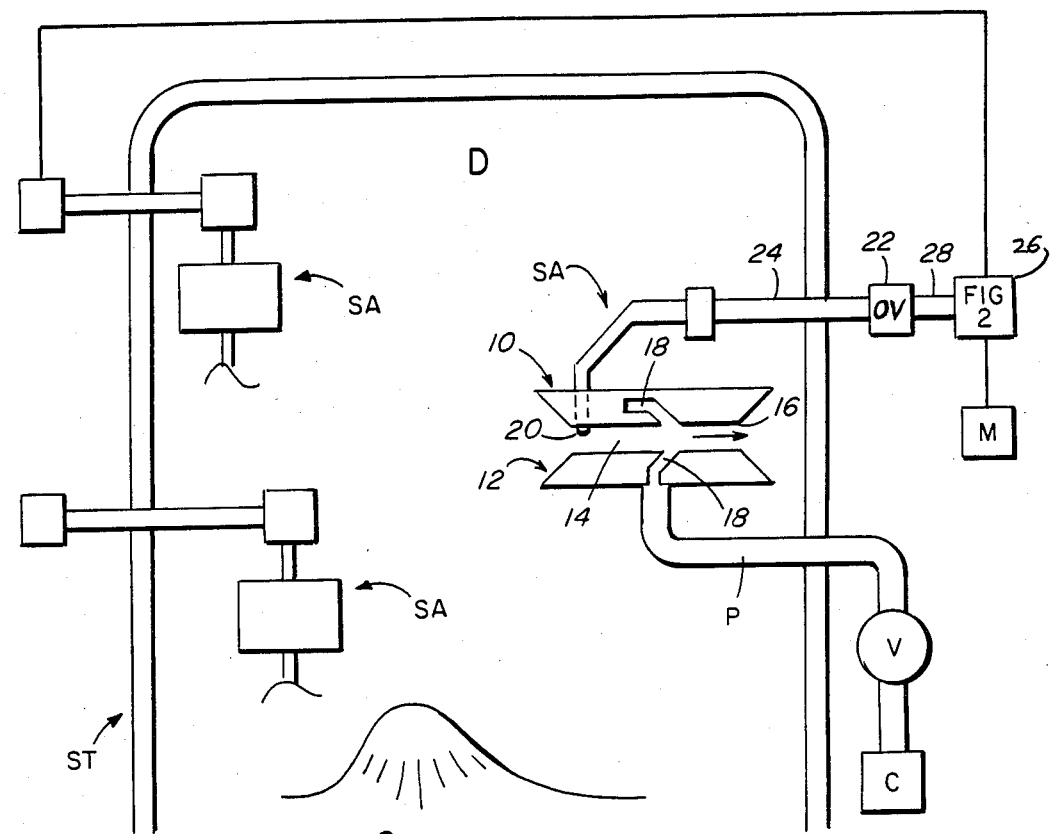
FIG. 1 is a cross-section sketch of a sensor assembly forming part of a preferred embodiment of the invention; and, FIG. 2 is a block diagram of the circuit for processing the signal from FIG. 1 sensor.
Figure 3:
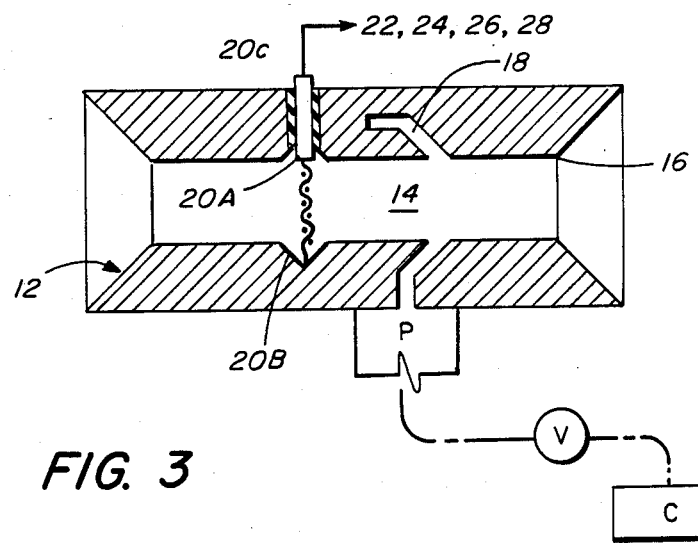

FIG. 1 shows a storage elevator ST containing a piled particulate substance G, e.g. grain with an overhead inevitable dust environment D. A series of sensor assemblies SA, are distributed in volume D for mapping dust concentration. Each sensor assembly comprises a venturi nozzle 10 with an inlet converging section 12, a throat 14, a diverging outlet section 16. An annular flow channel 18 feeds compressed gas (from a source C via a pipe P and control valve V) to the interior of the venturi to create an annular high speed flow which stays along wall of throat 14 by Coanda effect and creates a suction drawing dust-laden air from volume D through the interior of the nozzle.

A sensing electrode 20 is inserted in the nozzle and connected to circuit element 26 via shielded cabling 24. An overvoltage protector 22 ("OV") is provided to protect the measuring 26 elements. The flow of compressed gas through the annular channel 18 causes ambient dust D to be sucked into converging section 12 and impinge on sensor 20 therefy creating a triboelectric signal. Further cabling 28 connects various such assemblies to control and signaling apparatus. The apparatus opens vents, start and stop filling, etc. and/or alarm A. An optional analog voltage signal may be employed to operate a meter M as an indication of dust level at the sensor.

The air flow through the sensor assembly has a velocity over the electrode of 2,000 to 3,000 ft./min. which insures good sensitivity to dust particles in the atmosphere surrounding the sensor as well as preventing the build up of material around the electrode. The electrode is placed upstream of the drive air inlet so that condensates or other contaminates in the drive air do not foul the electrode. Inlet blocked off pressure is $-0.5$ to $-1.5''$ H$_2$O and velocity 1 cm. from the inlet is 180–280 ft./M. Outlet blocked-off pressure is $+0.63$ to $+1.8''$ H$_2$O and velocity 1 cm. from the outlet is 1500–1900 ft./min.

Figure 2:
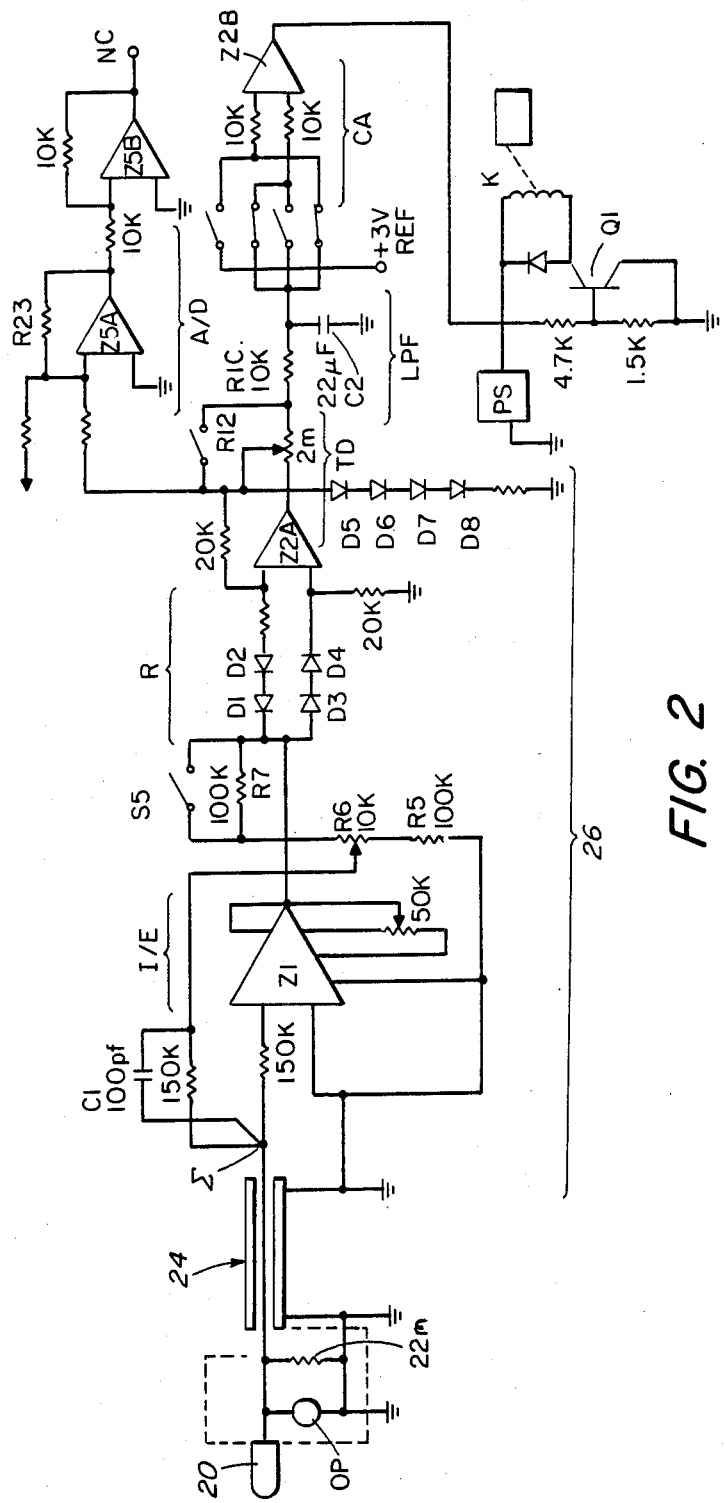

FIG. 2 is a diagram of the circuit for processing the signal from the sensor. The current resulting from the charge transfer at probe 20 is conducted through low noise coaxial cable 24 to current to voltage converter I/E comprising an operational amplifier Z1, which converts the current signal into a voltage signal and provides amplification of $1 \times 10^{-8}$ to $1 \times 10^{-12}$, amperes per volt which is selectable in three adjustable ranges.

The rectifier stage R provides a unipolar signal regardless of the polarity of charge transfer occurring at the sensor probe. Time delay circuit TD smooths the inherently noisy signal from the rectifier R and is adjusted as required to prevent false alarming due to normal short term dust conditions. TD is adjustable from 0.5 to 20 seconds.

The comparator CA compares the signal from TD with a constant 3 volt reference, and when the signal exceeds the reference, relay K is energized. The relay contacts (two single pole double throw) are used to control fans, vents, alarms, etc.

An optional analog output circuit AO provides a $+0$ to 10 volt output at OC representing the level of dust concentration at the sensor probe.

The control circuit's front end elements are in a sensor probe connection box 42 and include a bleed resistor 22 or over-voltage protection device OPV (dependent upon sensitivity range) used to prevent voltage build-up on the probe if the cable 24 should become disconnected.

The current to voltage conversion circuit I/E provides a virtual ground summing junction (Σ) at the cable input. Two 150K resistors act to prevent damage to OP-AMP ZI and provide an intrinsically safe connection for the cable 24. A 100M ohm Feedback resistor in conjunction with a voltage divider comprising R5, R6, and R7, controls the conversion gain of the circuit. R6 provides 100 to 1 adjustment and R7 is controlled by S5 which provides an additional factor of ten. C1 acts to limit high frequency noise.

The rectified signal is passed via time delay means to signal level indicator circuits. Cascaded diodes D1 and D2 and D3 and D4 are employed to produce an approximate one volt dead band to allow for temperature induced zero offset of the converter circuit.

OP-AMP Z 2A provides a low impedance output to drive the time delay circuit TD which is comprised of R12, R13 and C2 and a signal level indicator circuit consisting of a LED D5 and diodes D6, D7 and D8 and R21. R12, R13, and C2 form a low pass filter LPF to smooth variations in the signal level at the output of Z2, with R13 providing a minimum time delay of 0.5 seconds and R12 being adjustable to provide a maximum delay of 20 seconds.

D6, D7 and D8 provide an additional threshold voltage for G so that a signal is not indicated until it reaches a level sufficient for alarm generation. Also shown in FIG. 2 is a schematic of the comparator circuit C which compares the signal at C2 and a 3 volt reference. When the signal exceeds the reference the output of Z2B changes from negative to positive causing transistor Q1 to energize relay K1.

The analog output circuit OA comprises OP AMP Z5A, in conjunction with C7, R22 and R23, form an averager circuit with a 1.5 second time constant to smooth the signal from the rectifier circuit. The averaging stage inverts the signal polarity; thus OP AMP Z5B is connected as an inverter to restore the signal polarity and provide a buffered positive output voltage signal at OC representing the dust loading at the sensor probe.

The active elements of the circuit are:
Z1—BURR-BROWN OPA-104CM
Z2—RCA CA3240E
Z3—NATIONAL SEMI-LM7812ACZ (NOT SHOWN)
Z4—NATIONAL SEMI-LM79LI2ACZ (NOT SHOWN)
Z5—RCA CA3240E
Q1—PN2222A The passive elements are shown on the drawing.

Further discussion of the control circuit is given in the application of Ronald L. Dechene and Robert E. Newton filed on even date herewith entitled FLOW MEASURING APPARATUS WITH ANALOG ESSENTIALLY LINEAR OUTPUT. The disclosure of said application (Ser. No. 658,587, filed Oct. 9, 1984) is incorporated herein by reference as though set out at length herein.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Apparatus for dust concentration detection in a gas volume comprising suspended dust particles comprising:
   (a) at least one means for converting a selected portion of the gas volume into a small cross-section i.e., less than one squ. in., fast gas stream of velocity of at least 1,000 feet per minute, said means comprising a gas flow inductor as a source of negative pressure,
   (b) means for creating a charge transfer and resultant electrical signal varying in relation to dust concentration in the gas stream,
   (c) the apparatus being constructed and arranged to provide a velocity-charge transfer match that produces a sensitive reading and avoids dust particle collection within the means for creating, and
   (d) apparatus wherein the means for converting comprises a gas flow inductor as a source of negative pressure, wherein the inductor comprises a Venturi with a throat and with annular inductor gas flow through a portion thereof downstream of the throat of said Venturi.

2. Apparatus in accordance with claim 1 wherein the means (b) for creating comprises an electrode probe in the inlet cross-section of the throat of said Venturi.

3. Apparatus in accordance with claim 1 wherein multiple units for creating are provided at distributed locations.

* * * * *